(12) United States Patent
O'Dwyer et al.

(10) Patent No.: US 6,223,590 B1
(45) Date of Patent: May 1, 2001

(54) VOLATILIZATION DEVICE FOR LIQUIDS

(75) Inventors: Barry O'Dwyer, Marlborough, NH (US); Christopher D. Prozzo, Athens, VT (US)

(73) Assignee: Janos Technology Inc., Townsend, VT (US)

(*) Notice: Subject to any disclaimer, the term of this patent is extended or adjusted under 35 U.S.C. 154(b) by 0 days.

(21) Appl. No.: 09/457,426

(22) Filed: Dec. 7, 1999

Related U.S. Application Data

(63) Continuation-in-part of application No. 09/015,601, filed on Jan. 30, 1998, now Pat. No. 6,006,591.

(51) Int. Cl.$^7$ .................................................. G01N 1/00
(52) U.S. Cl. ................... 73/64.56; 73/61.56; 73/864.81; 73/864.21; 73/863.03
(58) Field of Search ................... 73/1.05, 23.27, 73/64.56, 61.77, 64.44, 64.45, 64.46, 23.41, 53.05, 61.41, 61.55, 865.23, 863.43, 864.21, 864.81, 863.03; 62/125

(56) References Cited

U.S. PATENT DOCUMENTS

| | | | |
|---|---|---|---|
| 3,103,807 | * | 9/1963 | Broerman ............................ 73/23.42 |
| 4,644,807 | * | 2/1987 | Mar .................................... 73/863.23 |
| 4,999,164 | * | 3/1991 | Puchinger ......................... 73/863.23 |
| 5,044,166 | * | 9/1991 | Wijmans et al. ....................... 62/85 |
| 5,163,979 | * | 11/1992 | Patrick et al. ....................... 73/23.36 |
| 5,297,433 | * | 3/1994 | Elgas .................................. 73/64.56 |
| 5,469,714 | * | 11/1995 | Manz et al. ........................... 62/125 |
| 5,525,303 | * | 6/1996 | Ford et al. .......................... 73/61.52 |
| 5,611,846 | * | 3/1997 | Overton et al. .................... 73/23.36 |

\* cited by examiner

*Primary Examiner*—Hezron Williams
*Assistant Examiner*—Michael Cygan
(74) *Attorney, Agent, or Firm*—Herbert M. Wolfson

(57) ABSTRACT

The process is disclosed for transforming a liquid mixture sample in a pressurized container to a vapor phase sample of substantially the same concentration as in the liquid mixture which includes the combination of a coarse filter, a first orifice or pressure regulator device, a pressure cut-off switch or second pressure regulator, a coalescing filter, and a fitting for linking the device to an analytical device.

4 Claims, 1 Drawing Sheet

VOLATILIZATION DEVICE FOR LIQUIDS

CROSS REFERENCE TO RELATED APPLICATION

This application is a continuation-in-part of pending U.S. patent of application Ser. No. 09/015,601, filed Jan. 30, 1998 now U.S. Pat. No. 6,006,591.

BACKGROUND OF THE INVENTION

There is a continuing need to analyze containers of volatile mixtures, such as mixtures of fluorocarbon liquids and other lower boiling organic gas mixtures. The concentration of the components in the vapor space above such liquids does not always correspond to the concentration in the liquid state due to several reasons. One factor is due to Raoults Law which states that the vapor concentration of a component depends upon the molefraction of that component in the liquid states. A second factor is that the vapor represents a distillation of the components in the liquid state, and many times the distillation will represent an azeotropic distillation in which the concentration of components in the liquid will control the concentration in the vapor state. It is also true that layering can occur of components in the vapor state due to differing densities in the several gases.

Another method of achieving a gas whose composition is equal to that of the liquid in a container of volatile liquids is the evaporation of a quantity of the material which requires heat and gives a gas of uncertain pressure values, is more difficult to carry out in a precise fashion and obtain correct analytical results, nor does such a method remove the oil which will be present in a quantitative fashion.

The invention described below precludes these sorts of complexities and gives every time an analysis of the liquid state which is not skewed by any known factors on a gas at a known pressure.

SUMMARY OF THE INVENTION

The device of this invention is comprised of a number of components connected in series, the purpose being to transform a liquid sample under pressure in the liquid container into an oil and particulate-free gas sample at a predetermined known pressure. The components are sequentially:

1. a coupler which attaches to the liquid part of the container;
2. a 20–50 micron sintered filter which removes relatively large inert particles;
3. a first orifice or pressure regulator which governs the free expansion of the liquid to a gas of identical composition. At the same time the gas is generated from the liquid sample, the oils usually present in such containers are converted into non-volatile droplets. The driving force in this evaporation is the pressure in the initial liquid container;
4. immediately following the gas expansion first orifice or pressure regulator there is a pressure negative shut off which will yield a steady flow of the gas to be analyzed through the gas cell contained in the IR filter spectrometer where the analysis is carried out;
5. in the next stage of the device there is a disposable coalescing filter which removes the oil droplets from the gas stream. Herein contained in the filter is an oil saturation color detector which is a dye. The development of an indicator color indicates the filter has exhausted its capacity and should be replaced. A viewport is present in this section of the device to make for ease of determination of the filter status; and
6. the final section is a fitting which is utilized to attach the volatilization device to the IR filter spectrometer employed for the analysis of the gas.

The device can be cleansed of all gases and be at ready to perform the next analysis by passing clean air through the device.

DETAILED DESCRIPTION OF THE INVENTION

Figure 1:
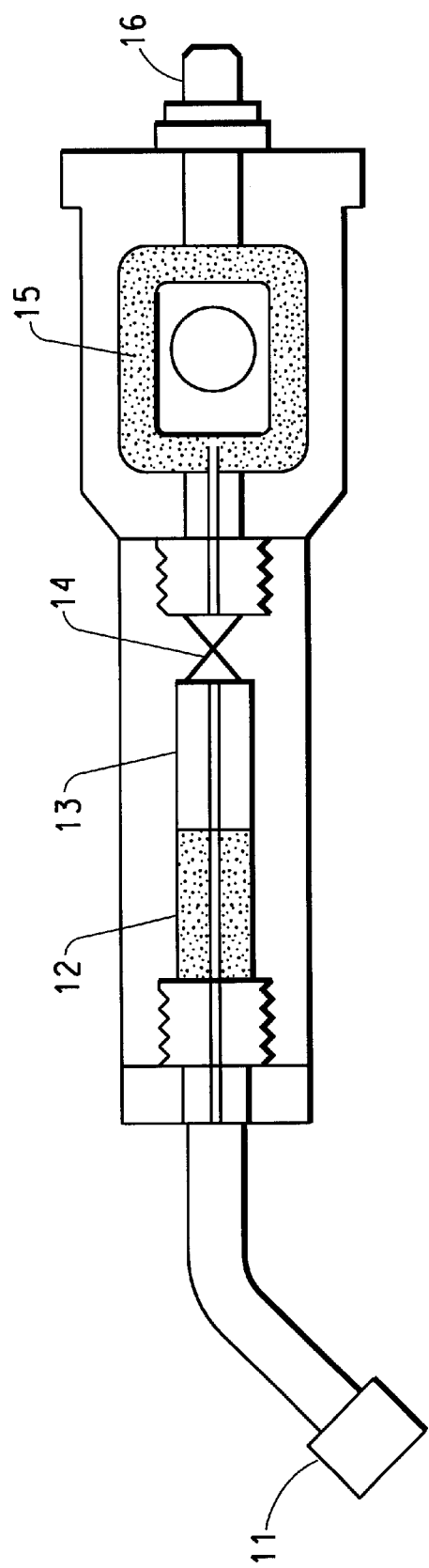
FIG. 1 is a schematic cross-sectional side view of the apparatus of the invention.

FIG. 1 designates the critical components of the device to transform a volatile liquid sample to a gas sample of identical composition.

Commonly, such a device would be useful for the analysis of pressurized containers of fluorocarbon liquids, but also applicable to other simple or complex volatile liquid compositions.

In FIG. 1, 11 designates the quick coupler which connects the vaporization device to the pressurized fluorocarbon liquid container, 12 indicates the sintered filter which is included to remove coarse particles from the liquid stream, prior to the first orifice or pressure regulator 13. The first orifice or pressure regulator 13 causes the free expansion of the liquid fluorocarbon which is under pressure, to yield a single or multi-component gas.

In this section of the device is a second pressure regulator 14, with negative shutoff to give a stream of gas at a standard pressure, suitable for filling the gas cell of an attached IR gas analyzer.

The penultimate component of the volatilization device is a disposable coalescing filter 15 to remove aerosols of any oils or non-volatile components in the original liquid contained in the pressurized container.

The final component is a suitable connector 16 to accomplish connection to the IR gas analyzer used to furnish an analysis of the gas mixture.

Alternatively, the first pressure regulator can be replaced by an orifice. Also, the first orifice or pressure regulator dimension can be optimized with respect to the vapor pressure of investigated liquid sample.

What is claimed is:

1. A method for analyzing a liquid-phase sample of component(s) of specific molar concentrations which comprises the steps, in sequence, of:

a) passing said liquid-phase sample into a pressurized container, the pressure being sufficient to maintain the sample in the liquid phase;

b) permitting said liquid sample to leave said pressurized container and pass through a pressure regulator adjusted to permit controlled expansion of said liquid-phase sample to a vapor-phase sample having substantially the same molar concentrations as in the original liquid-phase sample;

c) passing said vapor phase sample from step (b) through a second pressure-regulator to convert the pressure of said vapor phase sample to a standardized pressure; and d) analyzing said vapor phase sample at the standardized pressure whereby the specific molar concentrations of the components in the original liquid-phase sample are determined with substantial accuracy.

2. A method as in claim 1 wherein said liquid-phase sample is a sample of liquid refrigerant of components displaying a high vapor pressure.

3. A method as in claim 1 wherein the original liquid-phase sample is composed of fluorocarbon compounds useful as refrigerants.

4. A method as in claim 1 wherein said liquid-phase sample is passed through a filter to remove any solids present in said sample before step (b) is performed.

* * * * *